(12) United States Patent
Schwindt

(10) Patent No.: US 9,006,141 B2
(45) Date of Patent: Apr. 14, 2015

(54) PROTECTIVE LAYER FOR PLANTS AND TREES, THE PRODUCTION THEREOF AND USE THEREOF

(75) Inventor: Sascha Schwindt, Saarbrücken (DE)

(73) Assignee: Stiftung Nano Innovations, Olten (CH)

( * ) Notice: Subject to any disclaimer, the term of this patent is extended or adjusted under 35 U.S.C. 154(b) by 589 days.

(21) Appl. No.: 12/747,956

(22) PCT Filed: Oct. 29, 2008

(86) PCT No.: PCT/DE2008/001753
§ 371 (c)(1),
(2), (4) Date: Jul. 8, 2010

(87) PCT Pub. No.: WO2009/074124
PCT Pub. Date: Jun. 18, 2009

(65) Prior Publication Data
US 2010/0275331 A1 Oct. 28, 2010

(30) Foreign Application Priority Data

Dec. 12, 2007 (DE) .......................... 10 2007 060 320

(51) Int. Cl.
*A01N 25/00* (2006.01)
*A01N 25/04* (2006.01)
*A01N 25/34* (2006.01)
*A01N 43/16* (2006.01)

(52) U.S. Cl.
CPC ............... *A01N 25/04* (2013.01); *A01N 25/34* (2013.01); *A01N 43/16* (2013.01)

(58) Field of Classification Search
CPC ....... A01N 43/04; A01N 43/16; A01N 51/00; A01N 53/00; A61K 9/5115
USPC ......... 800/295, 298; 47/1.01; 504/100, 116.1; 435/410
See application file for complete search history.

(56) References Cited

U.S. PATENT DOCUMENTS

| 5,122,377 A | 6/1992 | Miller et al. |
| 6,069,112 A | 5/2000 | Glenn et al. |
| 2003/0203980 A1 * | 10/2003 | Valdes ............................ 516/99 |
| 2007/0224233 A1 * | 9/2007 | Maekawa et al. ............. 424/409 |

FOREIGN PATENT DOCUMENTS

| CN | 1319338 A | * 10/2001 | ............. A01N 59/00 |
| DE | 102006008535 A1 | 8/2007 | |
| EP | 0747184 A2 | 11/1996 | |
| EP | 1825752 A2 | 8/2007 | |
| EP | 1826248 A1 | 8/2007 | |
| KR | 2002-0078175 | * 10/2002 | |
| KR | 20020078175 | * 10/2002 | ................. C08J 3/02 |
| WO | 9838848 A1 | 9/1998 | |
| Wo | WO 2007/036939 | * 4/2007 | |

OTHER PUBLICATIONS

Li et al (2005) Pest Management Science 61: 583-590.*
UNited States National Nanotechnology Initiative website.*
Hench and West (1990) Chemical Reviews 90 (1):33-72.*
Hench, L. et al. "The Sol-Gel Process," Chem. Rev., 1990, vol. 90, No. 1, pp. 33-72.*
Badawy, M. et al. "Fungicidal and Insecticidal Activity of O-Acyl Chitosan Derivatives," Polymer Bulletin 54, pp. 279-289 (2005).*
Database WPI Week 200226, Thomson Scientific, London, AN 2002-196458, XP002579664, pp. 1-7, Great Britan.

* cited by examiner

*Primary Examiner* — Susan McCormick Ewoldt
(74) *Attorney, Agent, or Firm* — Laurence A. Greenberg; Werner H. Stemer; Ralph E. Locher

(57) ABSTRACT

The invention relates to a method for producing a protective layer on a surface of a plant, to a protective layer for a surface of a plant, to a plant coated with said protective layer, to a composition for carrying out the method and for producing the protective layer, and to uses of said composition. According to the invention, a method is proposed, wherein at least one sol gel having nano-scale particles is formed by the hydrolysis of at least one precursor in water and at least one nano-scale layer of the sol gel is applied onto the surface of the plant. The protective layer according to the invention comprises a nano-scale $SiO_2$ layer, and the composition according to the invention comprises at least one $SiO_2$-producing substance.

14 Claims, No Drawings

PROTECTIVE LAYER FOR PLANTS AND TREES, THE PRODUCTION THEREOF AND USE THEREOF

OBJECT OF THE INVENTION

The invention relates to a method of production of a protective layer on a surface of a plant, to a protective layer for a surface of a plant, to a plant coated with said protective layer, to a composition for carrying out the method and for production of the protective layer and uses of said composition.

BACKGROUND OF THE INVENTION

Every year, agriculture globally suffers losses amounting to billions caused by plant pests, e.g. fungi or feeding insect pests, which attack and damage the leaves of useful plants. Until now these plant pests have been controlled with plant protectants, which according to the pesticide index (German Federal Office of Consumer Protection and Food Safety, as at 01.11.2007) belong to the areas:
  herbicides against weeds,
  insecticides against insect pests,
  fungicides against fungal pathogens,
  rodenticides against rodents,
  nematicides against nematodes (threadworms),
  acaricides against mites/arachnids,
  molluskicides against snails,
  bactericides against bacteria,
  agents against viroids,
  agents against viruses,
  agents for vine grafting and grafting on fruit-bearing and ornamental shrubs,
  agents for preventing damage by game,
  agents for wound sealing/wound treatment,
  growth regulators,
  agents for treating seeds and planting stock, and
  agents for soil disinfection All agents and substances have in common that they either stimulate the plant to be protected to suitable defensive measures or they kill the pests.

The plant leaf is, along with the shoot axis and the root, one of the three basic organs of higher plants and is known as the organ type phyllome. Leaves are lateral outgrowths on the nodes (nodi) of the shoot axis. The primary functions of the leaves are photosynthesis (synthesis of organic substances using light) and transpiration (water evaporation, important for nutrient uptake and transport). Leaves only occur with cormophytes, i.e. fern-like plants (Pteridophyta) and seed-bearing plants (Spermatophyta). Conversely, they are absent from mosses and algae, although leaf-like structures can form on their thallus, but these are only to be regarded as analogs of leaves. There is an enormous abundance of leaf shapes. In some cases, in the course of evolution leaf organs have also developed that no longer have anything to do with the original function of the leaf, namely photosynthesis and transpiration: for example petals, leaf thorns and leaf tendrils, and bud scales.

The leaf is sealed against the exterior with a boundary tissue, the epidermis, which consists of just one cell layer. The epidermis possesses on the outside a water-impermeable wax layer cuticle, which prevents unregulated evaporation. The cells of the epidermis do not as a rule possess any chloroplasts (the cell constituents in which photosynthesis takes place). Exceptions to this are the epidermis of hygro-, helo- and hydrophytes and sometimes shade leaves, but especially the guard cells of the stomata, which always contain chloroplasts.

The stomata serve for regulation of gas exchange, primarily the release of water vapor. According to the distribution of the stomata, a distinction is made between hypostomatic leaves (stomata on the leaf undersurface, commonest form), amphistomatic leaves (stomata on both leaf surfaces) and epistomatic leaves (stomata on the leaf top surface, e.g. in the case of floating leaves). The appendages formed by the epidermis are called hairs (trichomes). If subepidermal cell layers are also involved in formation, these are called emergences: examples are spines or colleters. The assimilating tissue is called mesophyll. It is generally divided into the palisade parenchyma located under the upper epidermis and the spongy parenchyma located under that. The palisade parenchyma consists of one to three layers of oblong, chloroplast-rich cells standing perpendicularly to the leaf surface. In the palisade parenchyma, the main task of which is photosynthesis, there are about 80 percent of all chloroplasts. The spongy parenchyma consists of irregularly shaped cells, which owing to their shape form large intercellular spaces. The main task of the spongy parenchyma is to provide aeration of the parenchymal tissue. The cells are relatively poor in chloroplasts. The vascular bundles are often located on the boundary between palisade and spongy parenchyma in the upper spongy parenchyma. The structure is the same as that of the vascular bundles in the shoot axis and is generally collateral. The vascular bundles branch off from the shoot axis and pass through the leaf stalk without rotation into the leaf blade. As a result the xylem faces the upper surface of the leaf, and the phloem faces the leaf underside. Large vascular bundles are often surrounded by an endodermis, which is called bundle sheath here. The bundle sheath controls exchange of substances between vascular bundle and mesophyll. The vascular bundles end blind in the mesophyll. The vascular bundle is thereby reduced more and more, i.e. first the sieve tubes become fewer and disappear, then in the xylem part only spiral tracheids remain, and these finally end blind. The whole leaf is as a rule so densely traversed with vascular bundles that no leaf cell is more than seven cells away from a vascular bundle. The resultant small fields between the vascular bundles are called areolae or intercostal fields. The function of the vascular bundles is to transport water and minerals into the leaf (via the xylem) and to transport photosynthesis products away from the leaf (via the phloem).

So far no methods are known that produce, as protection against fungi and insect pests, a layer of whatever kind at all on the plant surface or leaf surface. It has been assumed until now that a coating would impair the physiology of the plant leaf and therefore would damage the plant. A coating as plant leaf-protecting layer must therefore fulfill two conditions. On the one hand sufficiently high translucence is required, in order to supply the chloroplasts contained in the plant leaf with radiation in the range from 320 to 700 nm. A coating that adsorbs or reflects in this wavelength range would impair the energy supply of the plant cell. The stroma is located as plasma phase in the interior of the chloroplasts. This stroma is traversed by thylakoid membranes (membrane invaginations), which stacked roll-like on top of one another form the granum. The chlorophyll embedded as pigment in the membranes can now once again adsorb light from the aforementioned wavelength range and utilize the absorbed energy for the production of ADP (adenosine triphosphate) from ADP (adenosine diphosphate) and phosphate.

The second requirement that a nanoscale plant leaf-protecting layer must fulfill is undisturbed function of the stomata. The gas exchange of a plant takes place through the stomata (Greek stoma, mouth). The stomata are normally formed by two bean-shaped cells, the guard cells, which surround an opening, the stoma. If we also include the cells that are located around the guard cells, we talk of the stomatal apparatus (stomatal complex). The pores themselves are strictly speaking the actual stomata. Guard cells are as a rule located in the lower epidermis of plant leaves, in the case of grasses on both sides of the leaf, and in the case of floating-leaf plants only on the upper surface. Gas exchange with the surrounding air is important in particular for supply of $CO_2$. Carbon dioxide is absorbed by the plants from the air by the processes of photosynthesis. For optimum functioning of diffusion through the cell walls, these must be as thin and/or permeable as possible. However, such cells evaporate a lot of water, and with such leaves terrestrial plants would quickly wither. Through separation of the intercellular spaces in the leaf from the dry outside air by the stomata, the plant gains control over water loss. Other points are important for the stomata: evaporation (stomatal transpiration or evaporation) takes place through the pores, which produces suction, by which water is transported from the roots and into the leaves. With the water, nutrient salts are carried from the soil and are concentrated in the leaves. Additionally the evaporation cools the leaves, they do not overheat under strong insolation and the specific temperature optimum of the enzymes in the leaf tissues is not exceeded. The transpiration just over the area of the stomata, which only make up 1-2% of the total leaf surface area, is up to ⅔ of the evaporation, i.e. the resistanceless evaporation, of a water surface of equal area. Investigations have shown that many small openings at equal surface area evaporate more water. The reason is the so-called "edge effect": molecules at the edge of a stoma can also diffuse sideways, whereas those in the middle hamper each other. The proportion of cuticular transpiration is very small, with hygrophytes (plants in moist areas) with tender leaves less than 10% of the evaporation of a free water surface, with trees less than 0.5% and with cacti even only 0.05%.

The stomatal apparatus consists of two guard cells, as a rule bean-shaped cells, which adhere to one another at both ends. Between them there is an intercellular gap, the pore, which forms the link between outside air and respiratory cavity. In some plants the two guard cells are surrounded by specialized epidermal cells, the subsidiary cells (pale blue in the illustrations), which are involved indirectly in opening and closing of the stoma. Leukoplasts can often be seen in the subsidiary cells. The guard cells contain chloroplasts, and so can carry out photosynthesis. The extent of opening of the pore is variable, in sunlight and with sufficient supply of water they are as a rule wide open, at night or with lack of water they are closed.

SUMMARY OF THE INVENTION

The invention is based on the problem of making available a method of production of a protective layer on a plant, a protective layer for plants and a composition for carrying out the method and for production of the protective layer, which prevent parasitic plant pests such as fungi and insect pests from extracting nutrients from the plants or damaging them in some other way.

The problem is solved according to the invention by a method in which at least one sol-gel with nanoscale particles is formed by hydrolysis of at least one precursor in water and at least one nanoscale layer of the sol-gel is applied on the surface of the plant. The problem is further solved with a protective layer for a surface of a plant, which was produced according to this method. Furthermore, the problem is solved with a protective layer for a surface of a plant, in particular a leaf-protecting layer and/or a wood-protecting layer, which comprises a nanoscale $SiO_2$ layer. The problem is also solved with a composition that contains at least one $SiO_2$-producing substance.

Surface of a plant in the sense of the invention is to be understood as all plant parts or cavities that are in contact with the environment. The term plants comprises in this context all developmental stages and manifestations of a plant, including the seeds, seedlings, buds, leaves, blossoms, fruit and bark.

Surprisingly it was found that according to the invention a nanoscale barrier layer is formed on the surface of the plants, which does not impair the above described physiological processes such as photocatalysis and transpiration of water. The protective layer according to the invention does not for example affect the function of the stomatal apparatus, because the layer at a layer thickness of only approx. 100 nm does not seal the stomata with a diameter of approx. 0.015 to 0.03 mm and does not hamper the opening or closing process. At the same time it prevents the haustoria of molds, such as e.g. True Mildew (ascomycete of the family Erysiphaceae) penetrating through the barrier layer and tapping the sap as a source of nutrients. Fungi cannot form any mycelia on the protective layer, which penetrate through the stomata and into the interior of the leaf and would be able to form mycelium intercellularly. Insect pests, which also feed on sap, are unable to penetrate the barrier layer with their mouthparts. In contrast, the protective layer according to the invention is permeable without restriction for the photosynthetically usable radiation in the wavelength range from 320 nm to 700 nm, so that ATP production is not restricted or blocked. Moreover, the protective layer according to the invention does not constitute a diffusion barrier, so that the necessary gas exchange of the plant leaf through the stomata is not impaired. The protective layer according to the invention and/or the method according to the invention therefore also protect commercial and structural timber in the sense of DIN 68 800 against loss of value or destruction by fungi and insects. Another advantage of the solution according to the invention is that for initiation of the sol-gel process taking place on the plant surface, no plant-damaging activation energy in the form of heat supply is required and an atmospheric ambient temperature in the range from 5° C. to 35° C., preferably 10° C. to 25° C., is sufficient. In addition, the $SiO_2$ on the plant surface is available as plant fertilizer after the plant has died and rotted.

A nanoscale, respiration-active, organically modified coating based on $SiO_2$ produced by a modified sol-gel process, with biocidal active substances incorporated therein, the production of said coating, the further processing of the coating and use thereof as plant-protecting layer on seeds, seedlings, leaves, blossoms, fruits and bark of plants and trees, are preferred according to the invention.

In an especially advantageous embodiment of the invention it is envisaged that before applying the sol-gel on the plant surface, at least one antimicrobial active substance, which preferably has been dissolved and/or dispersed in a hydrophilic solvent, is added to the sol.

In another advantageous embodiment of the invention it is envisaged that the precursor is selected from the group comprising the alkyltriethoxysilanes and/or the aminopropyltriethoxysilanes. Up to 20 wt. % $Al_2O_3$, $TiO_2$, $ZrO_2$, MgO and/or $V_2O_5$, relative to the total proportion of $SiO_2$, can be added to the precursor.

In an especially advantageous embodiment of the invention it is further envisaged that the formation of the sol-gel is carried out within 24 hours at 20° C.

Preferably the application of the sol-gel on the surface of the plant takes place by contacting the surface with the dissolved precursor, in particular by spraying, dipping, spreading, painting, watering, film watering and/or spray bar, in particular with at least one spraying nozzle.

For intensification of the antimicrobial, especially fungicidal action of the plant leaf-protecting layer, antimicrobial active substances can be mixed with the $SiO_2$ matrix. Antibacterial or antimicrobial active substances can be used for destruction or growth inhibition of bacteria, fungi, algae and viruses and for protection against microbial contamination. The environmentally determined microbial contamination by approx. 2 to 3 billion different microorganisms, including approx. 15 000 that are spread through the air and therefore can colonize almost any surface, represents a continuously increasing potential health risk. In the following the term "antimicrobial" is used for the action of the substances, meaning the biocidal or biostatic action on microorganisms. The supply of antimicrobial active substances is not, however, absolutely essential, but depends on the species of phytopathogens to be expected.

As antimicrobial active substances, inorganic chemicals and metal compounds such as e.g. silver zeolite (Kanedo), silver silicate, silver sulfonate and silver metal, titanium oxide, soluble glass powder with metal ions, iron phthalocyanate, copper sulfonate, zinc-pyrithione; organosilicones such as e.g. organic silicone with ammonium salt: octadecyldimethyl-(3-(trimethoxysilyl)-propyl)-ammonium chloride; quaternized ammonium salts, such as e.g. didecyldimethylammonium chloride, hexadecylpyridinium chloride, cetyldimethylbenzylammonium chloride, polyoxyalkyltrialkylammonium chloride; surfactants, such as e.g. amphoteric surfactant: alkyldi(amino-ethyl)glycine, nonionogenic surfactant: glycerol stearate; guanidine such as e.g. 1,1-hexamethylene-bis-5-(4-chlorophenyl)-biguanide-digluconate, polyhexamethylene-biguanide hydrochloride; phenols such as e.g. Biozol, thymol, alkylene bisphenol-sodium salt, p-chloro-m-xylenol (PCMX), 5-chloro-2-(2,4-dichlorophenoxy)-phenol (Triclosan); anilines such as e.g. 3,4,4-trichlorocarbaniline, imidazoles such as e.g. 2-(4-thiazolyl)-benzimidazole, 2-(thiocyanomethylthio)-benzothiazole (TCMTB); natural products such as chitosan, propolis, hinokitol; carbohydrates such as e.g. neomycin sulfate, esters such as e.g. diethylphthalate, parabens, are used (see DE1020068534 and DE1020068535).

Sol-gel layers can be produced by a sol-gel process. Metal oxide xerogels from $SiO_2$, $R\text{—}SiO_n$, $R_2SiO_n$, $Al_2O_3$, $ZrO_2$, $TiO_2$ or their mixtures are preferably used, where R=H, alkyl, aryl, epoxy-alkyl, aminoalkyl and n can be 1.5 or 1. These gels are obtained by hydrolysis and condensation reactions of silicon alkoxides. In this, the molecules are joined together owing to the polymerization that took place during the process. The total volume of the sols is thus polymerized. The polymerized silicon oxides form an $SiO_2$ gel. Continuing condensation with alcohol cleavage leads to a spherical accretion of the particles, which starting from a thickness of approx. 70 nm can be detected from the light scattering on the particles (Tyndall effect). By a process designated as gelation, sols can be converted into gels. The particles continue to grow, until they touch one another and, through further condensation, crosslink with one another. Finally a solid phase forms, which is imbued with a liquid phase. Gels are defined as dimensionally stable, easily deformable, liquid-rich disperse systems, which consist of a solid, irregular three-dimensional network and a liquid.

The protective layer according to the invention comprises a nanoscale $SiO_2$ layer. This $SiO_2$ layer preferably has a thickness of 50 to 300 nm, especially preferably between 80 and 150 nm or between 120 and 250 nm.

In an advantageous embodiment of the invention the protective layer has an elasticity of up to 250% and undergoes longitudinal growth as an intact protective layer, so as not to impair plant leaf growth in the growth phase of relevance for attack by molds and insect pests.

The solvent for the sol, which forms the protective layer on the leaf surface by the sol-gel process, is preferably water ($H_2O$).

The $SiO_2$ matrix of the protective layer according to the invention can moreover advantageously, owing to its $Si^{2+}$ charge, have an antimicrobial action through ion exchange processes.

For functionalization, on the one hand aliphatic and aromatic aldehydes, carboxylic acids or aminocarboxylic acids are added to the sol from tetraethoxysilane, trimethoxymethylsilane, or dimethoxydimethylsilane. Alternatively, by means of altered substituents on the precursor ($R'Si(OC_2H_5)_3$), the $SiO_2$ network is modified organically. The synthesis of various alkyltriethoxysilanes with azomethine bonding through the reaction of aminopropyltriethoxysilane with benzaldehyde derivatives or acetyl acetone is also used for this.

Inorganic-oxide gels are often produced by reaction of elemental alkoxides with alcohol-water mixtures or in pure water. In this, the alcohol serves for production of a homogeneous reaction mixture and can be replaced with other protic or aprotic solvents. The flexibility and porosity of the sol-gel layers can be varied by modification of the recipes. A higher proportion of $R\text{—}SiO_n$ and/or $R_2SiO_n$ improves the flexibility of the layers, through the formation of mixed oxides such as $Al_2O_3$, $ZrO_2$, $TiO_2$ the abrasion resistance and specific hardness can be increased.

According to a preferred embodiment the present invention relates to a composition of the aforementioned kind, for which the $SiO_2$-producing substance is selected from 0 to 100 wt. %, preferably 1 to 99 wt. % tetraethoxysilane,
0 to 100 wt. %, preferably 1 to 99 wt. % trimethoxymethylsilane,
0 to 100 wt. %, preferably 1 to 99 wt. % dimethoxydimethylsilane,
0 to 100 wt. %, preferably 1 to 99 wt. % polydimethylsiloxane,
0 to 100 wt. %, preferably 1 to 99 wt. % vinyltrimethoxysilane,
0 to 100 wt. %, preferably 1 to 99 wt. % 3-aminopropyltrimethoxysilane,
0 to 100 wt. %, preferably 1 to 99 wt. % 3-methacryloxypropyltrimethoxysilane and/or
0 to 100 wt. %, preferably 1 to 99 wt. % 3-glycidyloxypropyltrimethoxysilane.

According to a preferred embodiment the present invention relates to a composition of the aforementioned type, wherein the $SiO_2$-producing substance furthermore contains up to 20 wt. % $Al_2O_3$, $TiO_2$, $ZrO_2$, MgO and/or $V_2O_5$, these additives being present in any mixture proportions, preferably in mixture proportions between 0.1 wt. % and 50% wt. % from the group $Al_2O_3$, $TiO_2$, $ZrO_2$, MgO and $V_2O_5$, especially preferably in mixture proportions between 1 wt. % and 20 wt. % from the group $Al_2O_3$, $TiO_2$ and $ZrO_2$.

According to a preferred embodiment the present invention relates to a composition of the aforementioned type, wherein the halogenated dihydroxydiphenylmethane, -sulfide and -ether is selected from 5,5'-dichloro-2,2'-dihydroxy-diphenylmethane, 3,5,3',5'-tetrachloro-4,4'-dihydroxy-diphenylmethane, 3,5,6,3',5',6'-hexachloro-2,2'-dihydroxy-diphenylmethane, 5,5'-dichloro-2,2'-dihydroxy-diphenylsulfide, 2,4,5,2',4'5' hexachlorodihydroxy-diphenylsulfide, 3,5,3',5'-tetrachloro-2,2'-dihydroxy-diphenylsulfide, 4,4'-dihydroxy- 2,2' dimethyl-dipeylmethane, 2',2-dihydroxy-5',5-diphenyl ether or 2,4,4'-trichloro-2'-hydroxy-diphenyl ether.

Furthermore these are phenols in the $SiO_2$ matrix, the preferred group are the halogenated dihydroxydiphenyl-methanes, sulfides, and -ethers, which for example are selected from 5,5'-dichloro-2,2'-dihydroxy-diphenylmethane (Preventol DD, Bayer AG), 3,5,3',5'-tetrachloro-4,4'-dihydroxy-diphenylmethane (Monsanto Corporation), 3,5,6,3',5',6'-hexachloro-2,2'-dihydroxy-diphenylmethane (Hexachlorophene), 5,5'-dichloro-2,2'-dihydroxy-diphenylsulfide (Novex, Boehringer Mannheim), 2,4,5,2',4',5'-hexachloro-dihydroxy-diphenylsulfide, 3,5,3',5'-tetrachloro-2,2'-dihydroxy-diphenylsulfide (Actamer, Monsanto), 4,4'-dihydroxy-2,2' dimethyl-dipeylmethane, 2',2-dihydroxy-5',5-diphenyl ether (Unilever), 2,4,4'-trichloro-2'-hydroxy-diphenyl ether (Irgasan DP 300, Ciba-Geigy).

According to a preferred embodiment the present invention relates to a composition of the aforementioned type, wherein the phenol is 2,4,4'-trichloro-2'-hydroxy-diphenyl ether.

Especially preferred here are the halogenated dihydroxy-diphenylmethanes and here in particular 2,4,4'-trichloro-2'-hydroxy-diphenyl ether (Triclosan), which is already used in many other products and has been investigated sufficiently for its toxicity to humans.

Furthermore, as active substances, substituted quaternary ammonium salts of alkylated phosphoric acid are used, whose biostatic action has been documented in numerous publications. Owing to the very good water solubility of these salts, their incorporation in the $SiO_2$ matrix is especially advantageous. Also halogenated quaternary ammonium salts such as cetyltrimethylammonium bromide have provided evidence of their antimicrobial action and can be used in the $SiO_2$ matrix.

The mixture proportions of the antimicrobial active substances chitosan, 2,4,4'-trichloro-2'-hydroxy-diphenyl ether (Triclosan) and quaternary ammonium salts in the sols relative to one another is also of importance. In total the antimicrobial active substances can make up between 0.1 wt. % and 50 wt. %, preferably 1 to 20% relative to the total composition of the sols. The proportion of the particular antimicrobial active substances can then be between 1 vol. % and 98 vol. %. By means of different recipes (quantitative proportions) the antimicrobial action can be adjusted to the particular mold population for the purpose of greatest action.

According to a preferred embodiment the present invention relates to a composition of the aforementioned type, wherein it relates to cationic, anionic or nonionic deacetylated chitosans and chitosan derivatives, preferably trimethyl chitosanium chloride, dimethyl-N-$_{C.\ to\ C}$-alkyl chitosanium iodide, quaternary chitosan salts with anions of phosphoric acid, O-carboxymethylchitin-sodium salts, O-acylchitosan, N,O-acylchitosan, N-3-trimethylammonium-2-hydroxypropyl-chitosan and O-TEAE-chitin iodide.

According to a preferred embodiment the present invention relates to a composition of the aforementioned type, wherein the chitosans and chitosan derivatives are low-molecular chitosans and chitosan derivatives, the molecular weights being between $1.0 \times 10^5$ g/mol and $3.5 \times 10^6$ g/mol, preferably between $2.5 \times 10^5$ g/mol and $9.5 \times 10^5$ g/mol.

According to a preferred embodiment the present invention relates to a composition of the aforementioned type, wherein it relates to quaternary ammonium salts of alkylated phosphoric acid, with each of the alkyl residues, independently of one another having 1 to 12 carbon atoms and/or halogenated ammonium salts, preferably cetyltrimethylammonium bromide, didecyldimethylammonium chloride, hexadecylpyridinium chloride and polyoxyalkyltrialkylammonium chloride.

According to a preferred embodiment the present invention relates to a composition of the aforementioned type, wherein the microbial active substances are present in mixture proportions between 0.1 wt. % to 99.9 wt. %, preferably 1 to 99 wt. %, in particular 5 to 95 wt. %.

According to a preferred embodiment the present invention relates to a composition of the aforementioned type, furthermore containing usual excipients and additives, in particular acidic and basic polycondensation catalysts and/or fluoride ions.

The mechanical barrier effect of the protective layer according to the invention can be intensified by the combination of various biocidal active substances such as chitosan, 2,4,4'-trichloro-2'-hydroxy-diphenyl ether and quaternary ammonium salts.

The invention therefore relates to nanoscale, in particular 50 to 300 nm, preferably between 80 and 150 nm thick diffusible plant leaf-protecting layers, tree leaf-protecting layers and wood protecting layers, containing an organically modified porous $SiO_2$ layer, which is produced as barrier layer by a sol-gel process on the plant leaf surface, which cannot be penetrated by haustoria of molds and mouthparts of insects and can contain antimicrobial active substances.

According to a preferred embodiment the present invention relates to a coating of the aforementioned type, wherein the antibacterial active substance is selected from at least 2 compounds of the 3 following classes of compounds in the form of cationic, anionic or nonionic deacetylated chitosans and chitosan derivatives and/or phenols of the group of the halogenated dihydroxydiphenylmethanes, -sulfides, and -ethers and/or substituted quaternary ammonium salts of alkylated phosphoric acid.

According to a preferred embodiment the present invention relates to plant leaf-protecting layers, tree leaf-protecting layers and wood protective layers of the aforementioned type, wherein the halogenated dihydroxydiphenylmethane, -sulfide and -ether is selected from 5,5'-dichloro-2,2'-dihydroxy-diphenylmethane, 3,5,3',5'-tetrachloro-4,4'-dihydroxy-diphenylmethane, 3,5,6,3',5',6'-hexachloro-2,2'-dihydroxy-diphenylmethane, 5,5'-dichloro-2,2'-dihydroxy-diphenylsulfide, 2,4,5,2',4',5' hexachloro-dihydroxy-diphenylsulfide, 3,5,3',5'-tetrachloro-2,2'-dihydroxy-diphenylsulfide, 4,4'-dihydroxy-2,2' dimethyl-diphenylmethane, 2',2-dihydroxy-5',5-diphenyl ether or 2,4, 4'-trichloro-2'-hydroxy-diphenyl ether.

According to a preferred embodiment the present invention relates to a container sealing coating of the aforementioned type, wherein the phenol is 2,4,4'-trichloro-2'-hydroxy-diphenyl ether.

According to a preferred embodiment the present invention relates to a plant leaf-protecting layer, tree leaf-protecting layer and wood-protecting layer of the aforementioned type, wherein it relates to cationic, anionic or nonionic deacetylated chitosans and chitosan derivatives, preferably to trimethyl chitosanium chloride, -dimethyl-N-alkyl chitosanium iodide, quaternary chitosan salts with anions of phosphoric acid, O-carboxymethylchitin-sodium salts, O-acylchitosan, N,O-acylchitosan, N-3-trimethylammonium-2-hydroxypropyl-chitosan and O-TEAE-chitin iodide.

According to a preferred embodiment the present invention relates to a plant leaf-protecting layer, tree leaf-protecting layer and wood-protecting layer of the aforementioned type, wherein the chitosans and chitosan derivatives are low-molecular chitosans and chitosan derivatives, the molecular weights being between $1.0 \times 10^5$ g/mol and $3.5 \times 10^6$ g/mol, preferably however between $2.5 \times 10^5$ g/mol and $9.5 \times 10^5$ g/mol.

According to a preferred embodiment the present invention relates to a plant leaf-protecting layer, tree leaf-protecting layer and wood-protecting layer of the aforementioned type, wherein it relates to quaternary ammonium salts of alkylated phosphoric acid, wherein each of the alkyl residues, independently of one another has 1 to 12 carbon atoms and/or halogenated ammonium salts, preferably cetyltrimethylammonium bromide, didecyldimethylammonium chloride, hexadecylpyridinium chloride and polyoxyalkyltrialkylammonium chloride.

According to a preferred embodiment the present invention relates to a plant leaf-protecting layer, tree leaf-protecting layer and wood-protecting layer of the aforementioned type, wherein the antimicrobial active substances are present in any mixture proportions between 0.1 wt. % and 99.9 wt. %, preferably 1 wt. % to 99 wt. %.

According to a preferred embodiment the present invention relates to a plant leaf-protecting layer, tree leaf-protecting protecting layer and wood-protecting layer of the aforementioned type, wherein the $SiO_2$ layer consists at least partially of $R-SiO_n$, and/or $R_2-SiO_n$, where R=H, alkyl, aryl-, epoxy-alkyl- or aminoalkyl- and n=1.5 or greater.

According to a preferred embodiment the present invention relates to a plant leaf-protecting layer, tree leaf-protecting layer and wood-protecting layer of the aforementioned type, wherein the $SiO_2$ layer contains $Al_2O_3$, $TiO_2$, $ZrO_2$, MgO and/or $V_2O_5$ in any mixture proportions, preferably in mixture proportions between 0.1 wt. % and 50% wt. % from the group $Al_2O_3$, $TiO_2$, $ZrO_2$, MgO and $V_2O_5$, especially preferably in mixture proportions between 1 wt. % and 20 wt. % from the group $Al_2O_3$, $TiO_2$ and $ZrO_2$.

Preferably, through the provision and selection of a special quantitative range of an $SiO_2$-producing substance together with a special quantitative range of special active substances and of conversion to the $SiO_2$ matrix, a protective layer is created that has the aforementioned positive properties.

The invention further relates to the use of the composition according to the invention for coating leaves of plants from the families Vitaceae (grape-vine plants), Solanaceae (nightshade plants), Poaceae (grasses), Cucurbitaceae (pumpkin plants), Rosaceae (rose plants), *Oleaceae* (olive plants), Malvaceae (mallow plants), Ericaceae (heather plants), Palmaceae (palm), Lamiaceae (mint family) and/or Cannabeaceae (hemp plants), and the use of the composition according to the invention for coating the wood and/or the bark of trees of the genera spruce (*Picea*), larch (*Larix*), pine (*Pinus*), Douglas fir (*Pseudotsuga*), yew (*Taxus*), fir (*Abies*), juniper (*Juniperus*), oak (*Quercus*), chestnut (*Castanea*), ash (*Oleaceae*), robinia (*Robinia*), elm (*Ulmus*), walnut (*Juglandaceae*), cherry (*Prunus*), birch (*Betula*), alder (*Alnus*), lime (*Tilia*), poplar (*Populus*), beech (*Fagus*), willow (*Salix*), meranti (*Shorea*), mahogany (*Meliaceae*), teak (*Tectona*), balsa (*Ochroma*), jacaranda (*Dalbergia*), yellow balau (*Shorea*), bongossi (*Lophira*), obeche (*Triplochiton*), Bajam teak (*Intsia*), afzelia (*Afzelia*) and/or wenge (*Millettia*).

The invention also relates to the use of the composition according to the invention for controlling phytopathogens of the species true mildew, false mildew, foliar and tuber rot of the potato, foliar and brown rot of the tomato, tobacco blue mold, ergot, tobacco mosaic virus, fire-blight of pome fruit trees, shot-hole disease and/or elm disease.

The invention relates furthermore to the use of the composition, coating or protective layer according to the invention for coating seeds and/or seedlings of plants. It was found, surprisingly, that the composition, coating or protective layer according to the invention influences germination behavior and seedling development positively. The initial germination, i.e. appearance of the seedling root, of seeds that were coated with the coating according to the invention or treated with the composition according to the invention, takes place far more quickly. Also the secondary-leaf stage is reached more quickly with the plants or seeds or seedlings treated according to the invention, not least through the earlier germination. Furthermore, the absolute number of plants that develop is significantly increased compared with negative controls.

The invention moreover relates in particular to the use of the composition, coating or protective layer according to the invention for coating seeds and/or seedlings of plants of the families Vitaceae (grape-vine plants), Solanaceae (nightshade plants), Poaceae (grasses), Cucurbitaceae (pumpkin plants), Rosaceae (rose plants), *Oleaceae* (olive plants), Malvaceae (mallow plants), Ericaceae (heather plants), Palmaceae (palms), Lamiaceae (mint family) and/or Cannabeaceae (hemp plants), and/or the genera wheat (*Triticum*), rye (*Secale*), barley (*Hordeum*), rice (*Oryza*), maize (*Zea*), millet (*Sorghum, Panicum, Pennisetum*), oat (*Avena*), spruce (*Picea*), larch (*Larix*), pine (*Pinus*), Douglas fir (*Pseudotsuga*), yew (*Taxus*), fir (*Abies*), juniper (*Juniperus*), oak (*Quercus*), chestnut (*Castanea*), ash (*Oleaceae*), robinia (*Robinia*), elm (*Ulmus*), walnut (*Juglandaceae*), cherry (*Prunus*), birch (*Betula*), alder (*Alnus*), lime (*Tilia*), poplar (*Populus*), beech (*Fagus*), willow (*Salix*), meranti (*Shorea*), mahogany (*Meliaceae*), teak (*Tectona*), balsa (*Ochroma*), jacaranda (*Dalbergia*), yellow balau (*Shorea*), bongossi (*Lophira*), obeche (*Triplochiton*), Bajam teak (*Intsia*), afzelia (*Afzelia*) and/or wenge (*Millettia*).

The composition according to the invention or the protective layer according to the invention is thus suitable advantageously in particular for the strengthening of plants, plant parts or seeds and/or seedlings of these plants, in particular for increasing the number of secondary leaves and/or for the acceleration of growth.

EXEMPLARY DESCRIPTION OF ADVANTAGEOUS AND PREFERRED EMBODIMENTS OF THE INVENTION

Example of Application 1

1. Production of an Aqueous $SiO_2$ Sol-Gel 100 ml tetraethoxysilane, 400 ml water and 200 ml 0.01 N hydrochloric acid are mixed at ambient temperature (20° C.) and stirred continuously (approx. 5 hours). The result is an aqueous $SiO_2$ sol-gel, with a solids content of approx. 4.5% $SiO_2$ with an average particle size of 6 nm.

2. Production of an aqueous $SiO_2$ sol-gel, which produces a highly elastic nanoscale plant leaf-protecting layer.

40 ml tetraethoxysilane, 40 ml aminopropyltriethoxysilane and 20 ml 3-methacryloxypropyltrimethoxysilane, 400 ml water and 200 ml benzoic acid are mixed at ambient temperature (20° C.), wherein the $SiO_2$-forming precursors in the order tetraethoxysilane, aminopropyltriethoxysilane and 3-methacryloxypropyltrimethoxysilane after in each case 3 hours stirring are added to the solvent $H_2O$. Then, while stirring, the carboxylic acid is titrated. The result is an aqueous $SiO_2$ sol-gel with a solids content of approx. 6% $SiO_2$ with an average particle size of approx. 6 nm.

3. From 10 vines of the species "Noble Vine", 2 groups each with 5 plants were formed, and in each case 4 were sprayed with the above-described formulations using a compressed-air sprayer. Care was taken to produce a uniform film of moisture on the top surfaces and undersurfaces of the leaves. After 24 hours storage at room temperature and at air humidity of 55%, the vine leaves were dry and the polymerization of the precursors to a nanoscale $SiO_2$ layer of approx. 100 nm thickness was completed.

4. Then an aqueous solution with nutrients and ascomycetes of the species "*Plasmopara viticola*" was prepared and was sprayed on the leaf undersurfaces of the vines. After 10 days the leaves were examined. It was found that the reference vines without $SiO_2$ layer showed the typical phytopathogenic picture. The treated leaves showed no phytotoxic effects and only 2 of the 8 treated vines showed atypical small infections.

5. As the leaves showed the coloration of a normal disease-free plant and no indications of hydration could be discerned, it can be assumed that the absorption of $CO_2$ and the release of $O_2$ and $H_2O$ through the stomata were not impaired and the plants were fully capable of photosynthesis.

Example of Application 2, Wood-Protecting Layer

1. Production of an Aqueous $SiO_2$ Sol-Gel 100 ml tetraethoxysilane, 400 ml water and 200 ml 0.01 N hydrochloric acid are mixed at ambient temperature (20° C.) and stirred continuously (approx. 5 hours). The result is an aqueous $SiO_2$ sol-gel, with a solids content of approx. 4.5% $SiO_2$ with an average particle size of 6 nm.

2. Four pieces of wood were prepared from teak (*Tectona grandis*) with the dimensions 8×8×30 cm. 2 remained untreated and 2 were sprayed with the above-described sol-gel. In each case 1 untreated and 1 treated piece of wood was placed in the soil near a termite mound in Sri Lanka, in each case one treated and one untreated were left exposed in a marshy area in South India.

3. After 10 months' exposure time, the pieces of wood were dug up and examined. It was found that the two treated pieces of wood were absolutely intact and did not show any bite marks or feeding marks. The two untreated pieces of wood had each been eaten by termites by approx. 75% or 85%. The feeding channels in the wood could be attributed unambiguously to termites.

Example of Application 3, Antifungicidal Action on a Cork Surface

Another test of the antimicrobial action of the plant leaf-protecting layer was conducted by the Institut für Biotechnische Forschung und Entwicklung ("Institute for biotechnical research and development") Graf GmbH on cork surfaces and is described below.

Two differently coated and one uncoated bottle corks (material) were made available.

Sample designation 50/02/06-1: corks coated with composition according to example of application 1, formulation 1, marked with yellow thumbtack Sample designation 50/02/06-2: corks coated with composition according to example of application 1, formulation 2, marked with red thumbtack Sample designation 50/02/06-3: corks uncoated, unmarked From the surface of the corks, for the experiments an about 1 mm thick layer was separated in thin disks with a size of approx. 1 $cm^2$.

*Aspergillus flavus* DSMZ 62066, which originated from the Deutsche Sammlung für Mikroorganismen und Zellkulturen (German collection for microorganisms and cell cultures), DSMZ, Braunschweig, was used for the investigations. The culture was kept on ME at 8° C. Before use, the test microorganism was subcultured over at least 2 passages at least three days apart on ME (incubation at 30° C.). For determination of the fungicidal action on *Aspergillus flavus* according to ASTM E 2180-01, the cork materials were contaminated on their coated surface artificially with the test microorganism. The contamination of the test areas was carried out by applying in each case 50 μl of the microbial suspensions as agar film (in 0.3% agar-agar) on the test areas, which were stored horizontally for the test duration. After gelation of the agar films, the recoverable CFU were determined after 0 min (directly after gelation of the agar film) and after a further 4 and 24 hours. For this, the contaminated test materials were kept in screw-cap vessels with 5 ml "Microbe recovery medium" (TSB; equivalent to a dilution of $1\times10^{-2}$). The vessels were shaken vigorously on a vortex several times, to achieve maximum possible detachment of the microorganisms. Then determination of the CFU count was carried out, by plating final dilutions of $10^{-2}$ and $10^{-4}$ (in each case 0.1 ml) on ME plates and incubating them for 48 h at 30° C. In each case the CFUs determined in this "Microbe recovery medium" are shown in Table 2.

For each test organism and each material and each sampling timepoint, 3 parallel preparations (cork lamellae) were contaminated. The following control was also conducted: 50 μl of the microbial suspension (in 0.3% agar-agar) were transferred directly to a screw-cap test tube with 5 ml TSB and treated further as above; this provided information about the CFU density of the cell suspensions used for contamination, and about the efficiency of elutriation of the test areas.

Table 1 shows the CFU determined for the control. Table 2 shows the relative microbe survival rates on the different materials after different incubation times.

For determination of the fungistatic action on *Aspergillus flavus* (based on ISO Standard Method 846) the cork materials were contaminated artificially on their coated surface with the test microorganism.

TABLE 1

CFU (in each case in 100 μl of the stated dilution steps) of the controls.

| Dilution step | *Aspergillus flavus* |
|---|---|
| $10^{-4}$ | 137/145 |
| $10^{-6}$ | 0/1 |

TABLE 2

Microbe survival rates on coated and uncoated cork

| Material, incubation time | Microbe survival rate (for Table 2) |
|---|---|
| 50/02/06-1: corks with yellow thumbtack, 0 h | 93%* |
| 50/02/06-1: corks with yellow thumbtack, 4 h | 34% |
| 50/02/06-1: corks with yellow thumbtack, 24 h | 3% |
| 50/02/06-2: corks with red thumbtack, 0 h | 91% |
| 50/02/06-2: corks with red thumbtack, 4 h | 45% |
| 50/02/06-2: corks with red thumbtack, 24 h | 1% |
| 50/02/06-3: corks without thumbtack, 0 h | 85% |
| 50/02/06-3: corks without thumbtack, 4 h | 56% |
| 50/02/06-3: corks without thumbtack, 24 h | 34% |

*the CFU of the microbial suspension applied on the corks was set equal to 100%.

The contamination of the test areas was effected by applying in each case 50 μl of the microbial suspensions in glucose-mineral salt solution on the test areas, which were kept horizontal for the test duration. The contaminated cork lamellae were transferred to a mineral salt-agar plate and incubated at 30° C. The development of the mold mycelium was checked daily.

In tests on different cork surfaces significant differences appeared with respect to their fungicidal efficacy against *Aspergillus flavus*. The microbe recovery rate was satisfactory with all tested materials with a value of about 90% at timepoint 0 h. Over the test duration of 24 h on the coated corks there was a detectable reduction in recoverable CFU to about 1 to 3%, the uncoated cork sample showed a value of approx. 40%.

Example of Application 4, Stimulation of Seedling Development

Fiber-hemp seeds from a seed dealer were sprayed with distilled water (control) or the composition according to the invention until dripping. The seeds were then dried under a laminar-flow sterile bench, then this procedure was repeated once more. On the next day the dry seeds were sown in plastic trays filled with propagating soil. For this they were pressed in approx. 5 mm deep and covered with soil. To keep them moist the watered trays were kept in plastic dishes covered with a transparent cover. The greenhouse temperature was regulated to 24° C. during the day and 20° C. at night. On day 3 after sowing, germination was assessed. The key for assessment was recognizable presence of a seedling root.

In the rest of the experiment, over a period of 20 days the number of seedlings that had reached the secondary-leaf stage was determined. 12, 15, 16, 17, 18 Sep. and 1 Oct. 2007 were chosen as the assessment dates. For the plants treated with the composition according to the invention, after 20 days markedly increased numbers of seedlings were observed, being between 45% and 86% above the untreated control group. Also, the growth rate of the seedlings treated according to the invention was definitely improved. It was between 51% and 234% above the untreated control group.

An acceleration of germination or accelerated development of the seedlings in the early stage could be useful especially for growing districts with comparatively short vegetation periods.

The invention claimed is:

1. A method of coating a protective layer onto a surface of a seed or plant seedling, the method comprising the following steps:
   selecting a seed or plant seedling;
   forming at least one sol gel including nano scale $SiO_2$ particles from a coating solution having at least one $SiO_2$-producing substance, the sol gel being formed by hydrolysis of at least one precursor in water, the at least one $SiO_2$-producing substance participating in the hydrolysis as the at least one precursor and the $SiO_2$ producing substance additionally comprising 0.1 to 50 wt. % of at least one of $Al_2O_3$, $TiO_2$, $ZrO_2$, MgO, or $V_2O_5$ to the coating solution; and
   coating the sol gel onto a surface of the seed or plant seedling, an $SiO_2$ layer having a thickness of 50 to 300 nm being formed by further polymerization and condensation of the nano scale SiO2 particles, said layer has an elasticity of up to 250% and, wherein the coating accelerates germination of seeds and increases the number of secondary leaves of seedlings compared to uncoated seeds or seedlings.

2. The method of claim 1 wherein the $SiO_2$-producing substance is at least one of:
   0 to 100 wt. %, tetraethoxysilane,
   0 to 100 wt. %, trimethoxymethylsilane,
   0 to 100 wt. %, dimethoxydimethylsilane,
   0 to 100 wt. %, polydimethylsiloxane,
   0 to 100 wt. %, vinyltrimethoxysilane,
   0 to 100 wt. %, 3-aminopropyltrimethoxysilane,
   0 to 100 wt. %, 3-methacryloxypropyltrimethoxysilane, or;
   0 to 100 wt. % 3-glycidyloxypropyltrimethoxysilane,
   wherein each respective wt. % is based on a weight relative to percent composition of all components in said nano scale layer.

3. The method of claim 1, wherein between 1 wt. % and 20 wt. % of at least one of $Al_2O_3$, $TiO_2$, or $ZrO_2$ is added to the $SiO_2$ producing substance.

4. The method of claim 1, wherein the seed or seedling is selected from the group of Vitaceae, Solanaceae, Poaceae, Cucurbitaceae, Rosaceae, *Oleaceae*, Malvaceae, Ericaceae, Palmaceae, Lamiaceae, or Cannabeaceae.

5. The method of claim 1 wherein the nano scale layer of at least one $SiO_2$ layer has a thickness of 120 and 250 nm.

6. The method of claim 1 wherein the nano scale layer of at least one $SiO_2$ layer has a thickness of 80 and 150 nm.

7. The method of claim 1 wherein the $SiO_2$ layer further includes at least one of $R-SiO_n$, or $R_2-SiO_n$, wherein R is H, alkyl, aryl-, epoxy-alkyl, or aminoalkyl and n is 1.5 or greater.

8. The method of claim 1 wherein the $SiO_2$ layer further includes at least one anti-microbial active substance.

9. The method of claim 1 wherein the $SiO_2$ layer includes 0.1 wt. % to 50 wt. %, relative to the entire composition, of at least one anti-bacterial active substance having at least one of cationic, anionic, or non-ionic deacetylated chitosans and chitosan derivatives;
   at least one phenol from the group of halogenated dihydroxydiphenylmethanes, sulfides, and ethers; and substituted quaternary ammonium salts of an alkylated phosphoric acid.

10. The method of claim 1 wherein the $SiO_2$ layer includes an anti-bacterial active substance having at least two compounds of cationic, anionic, or non-ionic deacylated chitosans and chitosan derivatives or phenols from the group of halogenated dihydroxydiphenylmethanes, sulfides, and ethers; and
   substituted quaternary ammonium salts of an alkylated phosphoric acid.

11. The method of claim 9 wherein the halogenated dihydroxydiphenylmethane, sulfide, or ether is 5,5'-dichloro-2,2'-dihydroxy-diphenylmethane, 3,5,3',5'-tetrachloro-4,4'-dihydroxydiphenylmethane, 3,5,6,3',5',6'-hexachloro-2,2'-dihydroxydiphenylmethane, 5,5'-dichloro-2,2'-dihydroxydiphenylsulfide, 2,4,5,2'4',5' hexachlorodihydroxydiphenylsulfide, 3,5,3',5'-tetrachloro-2,2'-dihydroxydiphenylsulfide, 4,4'-dihydroxy-2,2' dimethyldiphenylmethane, 2'2-dihydroxy-5',5-diphenylether, or 2,4,4' trichloro 2'-hydroxydiphenylether.

12. The method of claim 9 wherein the phenol is 2,4,4'-trichloro-2'-hydroxydiphenylether.

13. The method of claim 9 wherein the chitosans and chitosan derivatives comprise at least one of trimethylchitosanium chloride, -dimethyl-N—C2 to C12 alkylchitosaniumiodide, quaternary chitosan salts with anions of phosphoric acid, O-carboxymethylchitin sodium salts, O-acylchitosan, N,O-acyl chitosan, N-3-trimethylammonium-2-hydroxypropyl-chitosan, and O-TEAE-chitin iodide.

14. The method of claim 1, wherein the seed or seedling is selected from the group of wheat, rye, barley, rice, maize, millets, oats, spruce, larch, pine, Douglas fir, yew, fir, juniper, oak, chestnut, ash, locust, elm, walnut, cherry, birch, alder, linden, poplar, beech, willow, meranti, mahogony, teak, balsa, rosewood, yellow balau, bongossi, obeche, merbau, *afzelia*, or wenge.

* * * * *